US006652442B2

United States Patent
Gatto

(10) Patent No.: US 6,652,442 B2
(45) Date of Patent: Nov. 25, 2003

(54) MICRO-ENDOSCOPE ASSEMBLY FOR INTRADUCTAL BRACHYTHERAPY OF A MAMMARY DUCT AND METHOD OF USING SAME

(75) Inventor: Dominick L. Gatto, Branford, CT (US)

(73) Assignee: Acueity, Inc., Palo Alto, CA (US)

( * ) Notice: Subject to any disclaimer, the term of this patent is extended or adjusted under 35 U.S.C. 154(b) by 0 days.

(21) Appl. No.: 10/127,664

(22) Filed: Apr. 23, 2002

(65) Prior Publication Data

US 2003/0199726 A1 Oct. 23, 2003

(51) Int. Cl.⁷ ............................................. A61N 5/00
(52) U.S. Cl. ................................................. 600/3
(58) Field of Search .............................. 600/106, 114, 600/153, 128, 1–8

(56) References Cited

U.S. PATENT DOCUMENTS

| | | | | |
|---|---|---|---|---|
| 1,406,509 A | * | 2/1922 | Viol | .............................. 600/7 |
| 3,335,109 A | | 8/1967 | Pines | |
| 4,323,055 A | | 4/1982 | Kubiatowicz | |
| 5,938,583 A | * | 8/1999 | Grimm | .............................. 600/7 |
| 6,179,766 B1 | * | 1/2001 | Dickerson | ..................... 600/1 |
| 6,221,622 B1 | | 4/2001 | Love | |
| 6,248,057 B1 | * | 6/2001 | Mavity et al. | ................ 600/3 |
| 6,500,114 B1 | * | 12/2002 | Petitto et al. | ............... 600/156 |
| 6,527,693 B2 | * | 3/2003 | Munro et al. | .................. 600/3 |

OTHER PUBLICATIONS

J.C. Blasko, et al., *The Urological Clinics of North America*, 23, "Should Brachytherapy be Considered a Therapeutic Option in Localized Prostate Cancer", pp. 633–650 (1996).
H. Ragde et al., *Cancer*, 80, "Interstitial Iodine—125 Radiation without Adjuvant Therapy in the Treatment of Clinically Localized Prostate Carconoma", pp. 442–423 (1997).

* cited by examiner

*Primary Examiner*—Samuel G. Gilbert
(74) *Attorney, Agent, or Firm*—Olson & Hierl, Ltd.

(57) ABSTRACT

The invention is directed toward a micro-endoscope assembly for intraductal brachytherapy comprising a cylindrical guide tube with a distal end defining an internal cylindrical passageway, a first smaller cylindrical tube eccentrically formed in the cylindrical passageway of a smaller diameter than said tube internal cylindrical passageway to receive and guide an endoscope, the smaller cylindrical tube forming together with an inner wall surface of the cylindrical guide tube a second passageway. A energy transmitting cartridge is mounted in the second passageway. The assembly is inserted into a mammary duct and the interior of the duct is viewed until the abnormality to be treated is determined in the duct. The container is deposited adjacent the abnormal tissue area in the duct and left in place to produce localized radiation or other forms of energy.

14 Claims, 3 Drawing Sheets

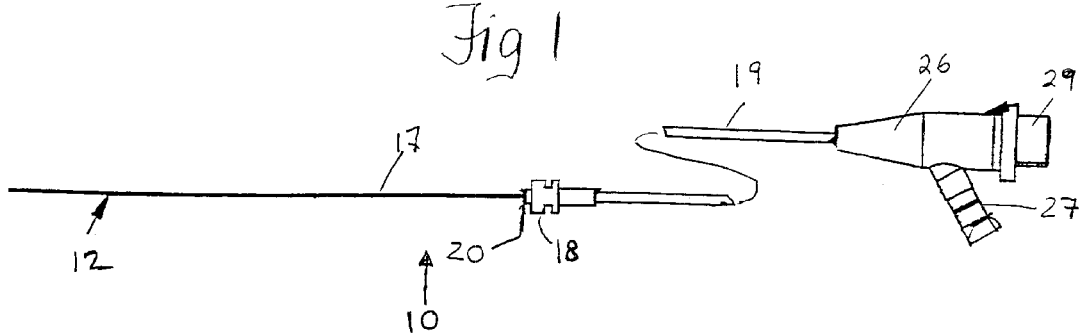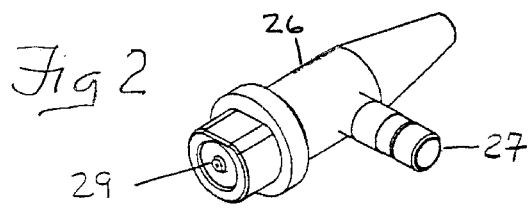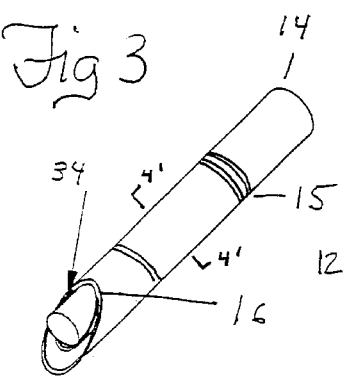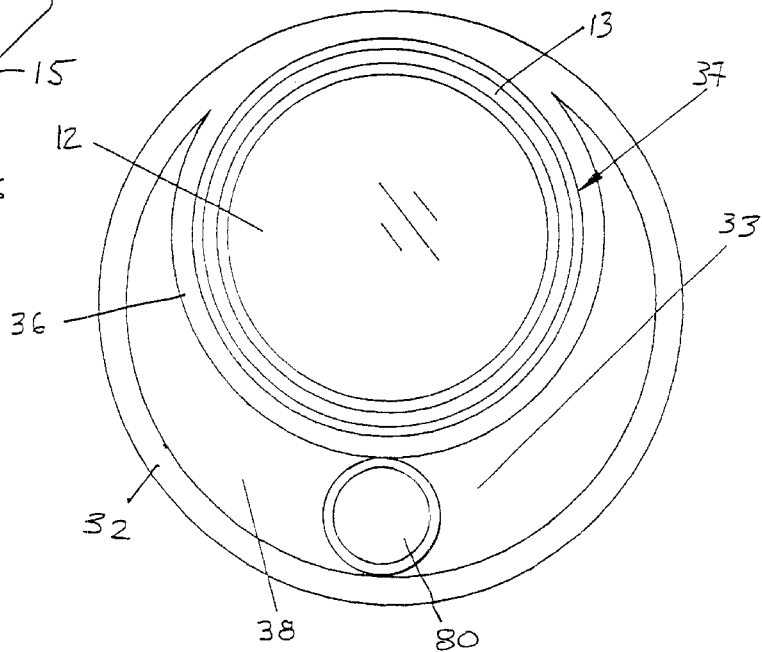

MICRO-ENDOSCOPE ASSEMBLY FOR INTRADUCTAL BRACHYTHERAPY OF A MAMMARY DUCT AND METHOD OF USING SAME

RELATED APPLICATION

There are no related applications.

FIELD OF INVENTION

The present invention is generally directed toward the treatment of breast cancer and more specifically toward the intraductal brachytherapy treatment of abnormal tissue and cells in the mammary breast ducts of women by placing a cartridge containing seeds or a construct which is treated to produce localized radiation via a cannula at the duct tissue site.

BACKGROUND OF THE INVENTION

A leading disease incurred by women is breast cancer. Breast cancer is the second leading cause of death for women of all ages and the leading cause of death for women aged 25–55 with approximately one in eight women incurring breast cancer in their lifetimes. Approximately 220,000 surgeries are performed annually in the United States with almost 20 percent requiring the complete removal of the breast. The current medical standard for determining breast cancer in women is mammography. For breast cancer detection, other than clinical examination and self-examination, women rely almost exclusively on mammography. It is estimated that more than 30 million mammograms are performed each year in the U.S. alone. Mammography is so insensitive that typically the average size of the tumor detected is ranges between 1 and 2 cms. At approximately 1.5 cm. size, a tumor has probably been growing, undetected, for nearly 8 years on average. In fact, two-thirds of mammographically detected breast cancer is invasive. In addition, mammography is notorious for "false positive" readings, which lead to many unneeded biopsies. However mammography fails to detect up to 20% of breast cancers in women over 50 and up to 40% of breast cancers in younger women.

Medical researchers have long recognized that nearly all breast cancer originates in the epithelial lining of the mammary duct system. Furthermore, it is well established that, in its early stages, most breast cancer develops very slowly and remains confined to the mammary ducts for up to 7–10 years. If these very early stages of premalignant and malignant disease could be detected and treated while the cancer is within the mammary duct system, the result would be a substantially better medical treatment outcome.

After detection breast cancer is generally treatable in three ways: surgery, radiation and chemotherapy. Surgery and radiation, of course, have risks and disadvantages well known to those skilled in the art. Chemotherapy also can be particularly disadvantageous as, for example, when the drugs involved cause sickness to the patient when they enter the blood stream.

Today's primary treatment of breast cancer is traditional surgery, either mastectomy or lumpectomy with radiation therapy. Surgery is, by definition, invasive and traumatic. Because the exact margins of cancerous growth are difficult to pinpoint, a surgeon may remove more breast tissue than is necessary or not remove enough.

Breast tumors are often treated with a combination of tumor removal (lumpectomy) followed by external beam radiotherapy to the whole breast. This has been found in several studies to result in the same cure rate as total breast removal. Surprisingly, only one third or so of women choose to keep their breast. One of the reasons for this low number may be that the external radiotherapy can take as long as 7 weeks to give, and this can be too much time away from home or work for some women.

Internal source radiation therapy (referred to as brachytherapy) places capsules of radioactive material inside the patient in proximity to the tumorous tissue. Brachytherapy is a general term covering medical treatment which involves placement of a radioactive source near a diseased tissue and may involve the temporary or permanent implantation or insertion of a radioactive source into the body of a patient. The radioactive source is thereby located in proximity to the area of the body which is being treated. This has the advantage that a high dose of radiation may be delivered to the treatment site with relatively low dosages of radiation to surrounding or intervening healthy tissue.

Dose and placement are accurately controlled by the physical positioning of the isotope. Cancer Treatment Centers of America has a treatment program that uses 5 days of brachytherapy (temporary radiation implant) instead of 5–7 weeks of external beam radiotherapy. This shorter time period is of a great benefit to all patients, but especially working women, those who live a distance away from a treatment center as well as those who just want to get the treatment over with as quickly as possible. So far, three hospitals in North America have published early results using similar techniques (Breast Brachytherapy). Each has so far reported a 98%–100% tumor control rate in the breast.

Some of the potential benefits of intraductal brachytherapy are:

1. The entire treatment takes days instead of weeks.
2. The radiation dose is concentrated in the area of the mammary duct where the DCIS is located thus less radiation will reach the skin, lungs, heart, ribs, the healthy part of the breast, and the body as a whole.
3. Because the treatment is so short, the intraductal brachytherapy can be given before chemotherapy is started (if chemotherapy is required). Radiation appears to be more effective if it can be given earlier rather than later.

Although brachytherapy is a proven treatment for cancer, using brachytherapy instead of external beam radiation for intraductal breast cancer is a recent idea. Benign conditions that can lead to abnormal intraductal assessment include intraductal papilloma, hyperplasia and atypical ductal hyperplasia and these can be removed without requiring invasive surgery. Likewise, hormonal therapies, and pharmaceutical agents (Tamoxifen) may control the growth of intraductal cancerous lesions. All women should have biopsies or intraductal samplings (lavage) that document the presence of atypia or malignant disease before an intraductal brachytherapy procedure is performed. The mammary duct should also be assessed by office ductoscopy to exclude the possibility of intraductal papiliomas, which can be treated with a simple resection. In addition, mama ductoscopy may reveal women who have multi-focal abnormal epithelia tissue and thus may be candidates for more extensive intraductal therapy.

Brachytherapy has been proposed for use in the treatment of a variety of conditions, including arthritis and cancer, for example breast, brain, liver and ovarian cancer and especially prostate cancer in men (see for example J. C. Blasko et al., The Urological Clinics of North America, 23, 633–650 (1996), and H. Ragde et al., Cancer, 80, 442–453 (1997)). Treatment may involve the temporary implantation of a radioactive source for a calculated period, followed by its subsequent removal. Alternatively, the radioactive source may be permanently implanted in the patient and left to decay to an inert state over a predictable time. The use of temporary or permanent implantation depends on the isotope selected and the duration and intensity of treatment required.

Examples of permanently implantable sources include Iodine-125 or Palladium-103 as the radioisotope. The radioisotope is generally encapsulated in a titanium casing to form a "seed" which is then implanted. Temporary implants for the treatment of prostate cancer may involve Iridium-192 as the radioisotope.

Conventional radioactive sources for use in brachytherapy include so-called "seeds", which are smooth sealed containers or capsules of a biocompatible material, for example of metals such as titanium or stainless steel, containing a radioisotope within a sealed chamber but permitting radiation to exit through the container/chamber walls (U.S. Pat. No. 4,323,055 and U.S. Pat. No. 3,351,049). Such seeds are only suitable for use with radioisotopes which emit radiation which can penetrate the chamber/container walls. Therefore, such seeds are generally used with radioisotopes which emit gamma.-radiation or low-energy X-rays, rather than with .beta.-emitting radioisotopes.

In brachytherapy, it is vital to the therapeutic outcome for the medical personnel administering the treatment to know the relative position of the radioactive source in relation to the tissue to be treated, to ensure that the radiation is delivered to the correct tissue and that no localized over or under dosing occurs. Current seeds therefore typically incorporate a marker for X-ray imaging such as a radiopaque metal (e.g. silver, gold or lead). Location of the implanted seed is then achieved via X-ray imaging, which exposes the patient to an additional radiation dose. Such radiopaque markers are typically shaped so that imaging gives information on the orientation as well as location of the seed in the body, since both are necessary for accurate radiation dosimetry calculations. Specifically, the dose distribution of the radiation is determined by the inverse square law and, accordingly, radiation effects on tissues at any distance from the radioactive source is limited. Nevertheless, brachytherapy is not amenable to tumors and cancers inaccessible by conventional surgical techniques.

Preferably, the insertion or implantation of a radioactive source for brachytherapy is carried out using minimally-invasive techniques such as, for example, techniques involving needles and/or catheters. It is possible to calculate a location for each radioactive source which will give the desired radiation dose profile. This can be done using knowledge of the radioisotope content of each source, the dimensions of the source, an accurate knowledge of the dimensions of the tissue or tissues in relation to which the source is to be placed, plus a knowledge of the position of said tissue relative to a reference point. The dimensions of tissues and organs within the body for use in such dosage calculations may be obtained prior to placement of the radioactive source by using conventional diagnostic imaging techniques including X-ray imaging, magnetic resonance imaging (MRI) and ultrasound imaging. However, difficulties may arise during the radioactive source placement procedure which may adversely affect the accuracy of the placement of the source if only pre-placement images are used to guide the source placement. For example, tissue volume may change as a result of swelling or draining of fluid to and from the tissue. Tissue position and orientation can change in the patient's body relative to a selected internal or external reference point as a result of for example manipulation during surgical procedures or movement of the patient. Thus, it is difficult to achieve accurate placement of sources to achieve a desired dosage profile in brachytherapy using only knowledge of tissue anatomy and position that was obtained prior to the placement procedure. Therefore, it is advantageous if real-time visualization of both the tissue and the radioactive source can be provided. During the implantation or insertion procedure, the location of the source may be inferred to be proximal to the tip of the device used for the procedure. However, the relative location of each separate radioactive source should be evaluated subsequent to the implantation procedure to determine if it is in a desired or undesired location and to assess the uniformity of the therapeutic dose of radiation to the tissue. Radioactive sources may migrate within the tissue following implantation. However, the relatively small size of current brachytherapy radioactive sources and the specular reflection properties of their surfaces makes them very difficult to detect by ultrasound imaging techniques, especially when they are orientated in directions other than substantially orthogonal to the incident ultrasound beam. Even very small deviations from relative to the incident ultrasound beam cause substantial reductions in the intensity of the echo signal.

Individual seeds may on rare occasions migrate within a patient's body away from the initial site of implantation or insertion. This is highly undesirable from a clinical perspective, for example as it may lead to under dosing of a tumor or other diseased tissue and/or exposure of healthy tissue to radiation. There is therefore also a need for radioactive sources for use in brachytherapy which show a reduced tendency to migrate within a patient's body when compared to conventional brachytherapy seeds.

Attempts have been made to provide an instrument which will allow the taking of tissue samples within small duct areas. A simple double barrel catheter with adjacent lumens is disclosed in U. S. Pat. No. 6,221,622 with one of the lumens being used to irrigate the milk duct of a breast and the other lumen being used to aspirate the fluid which has entered the duct allowing a continuous flow of saline through the duct which hopefully carries enough cells and tissues for a biopsy. Problems in the use of such an instrument include the small size required by the narrow small diameter lumens which can be blocked or limit the flow of fluid back through the aspiration lumen and thus preclude significant tissue collection or cause duct collapse. While the '622 Patent shows a small lumen size, the size problem is magnified when the other existing prior art is attempted to be applied to breast ducts because of the small size and thin cell walls of the mammary ducts.

Thus, there is a need in the art for new and better micro-cannula/endoscope assemblies and methods for using same that can be used to directly visualize the mammary ducts of a breast where visualization is by means of endoscopic devices, direct visualization (as opposed to creation of photographic images) to provide accurate placement of the brachytherapy cartridge. The present invention offers the additional advantage that the equipment required is comparatively simple to use and is less expensive than the equipment required to create photographic displays from such images.

SUMMARY OF THE INVENTION

The present invention is directed toward the detection and treatment of abnormal growths and cancer located in the mammary ducts of women's breasts which in the present invention is when the cancer is typically between two and three years old with a size of about 0.2 mm. This is over 50 times more sensitive than a standard mammogram According to the invention, an apparatus and a method is provided for intraductal brachytherapy of abnormal tissue found in the mammary duct using a micro-endoscope assembly having irrigation and aspiration capabilities. The micro-endoscope assembly includes a proximal actuation handle, an elongate flexible member extending from the proximal actuation handle and having an irrigation conduit.

The method comprises the steps of: inserting the cannula sheath in the duct of the breast of a woman, inserting the distal end of the micro-endoscope assembly into the sheath; viewing the inside of the duct as the distal end of the endoscope travels along the duct until a tissue abnormality is viewed; positioning the distal assembly proximate to a tissue to be treated; a temporary radiation implant (such as a seed) is placed into or onto the cancerous lesion (DCIS) in the duct. Either a radiation oncologist or breast surgeon may perform the procedure under direct visual guidance. The implants generate a low-dose-rate for an internal radiation treatment through the ducts. The implants are easily removed, and the patient will be able to go home on the same day. This will be performed on an outpatient basis. Patients will not be radioactive, and may do most of their usual activities during that period.

It is an object of the invention to allow physicians to perform a variety of intraductal cancer treatments with minimal or no discomfort for patients.

It is still another object of the invention to provide convenient, efficient, and economical mammary ductoscopy-breast care.

It is thus an object of the invention to provide a micro-endoscope assembly which can view the interior of a lactiferous duct to ascertain tissue abnormalities and deposit implants for intraductal brachytherapy.

It is yet another object of the present invention to provide for the intraductal brachytherapy of tissue with more precision and less trauma than by convention surgical procedures.

In brachytherapy procedures, large amounts of time are currently consumed loading radio active seeds and spacers into the brachytherapy needles. Further, once the needles are loaded, it becomes difficult to verify the dosage (i.e. number of seeds) or to check the level of radioactivity in any individual seed or seeds.

It would, therefore, be advantageous to design a brachytherapy seed or construct cartridge which decreases the time required to check dosage and radiation It another object of the invention to. design a brachytherapy seed or construct cartridge which facilitates loading of the cannula prior to the brachytherapy procedure.

It is another object of the present invention to provide a medical instrument of high durability which is easily cleaned and sterilized.

It is also an object of the micro-endoscope assembly invention to create a micro-endoscope assembly which can be easily handled by the physician for intraductal treatment.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 1 is an exploded side elevational view of the endoscope used in the present invention;

FIG. 2 is a perspective orientated view of the back end of the endoscope showing a light post;

FIG. 3 is a perspective view of a portion of the front end of the micro-endoscope assembly;

FIG. 4 is an enlarged cross sectional view taken along line 4'—4' on FIG. 3;

DETAILED DESCRIPTION OF THE INVENTION

Figure 5:
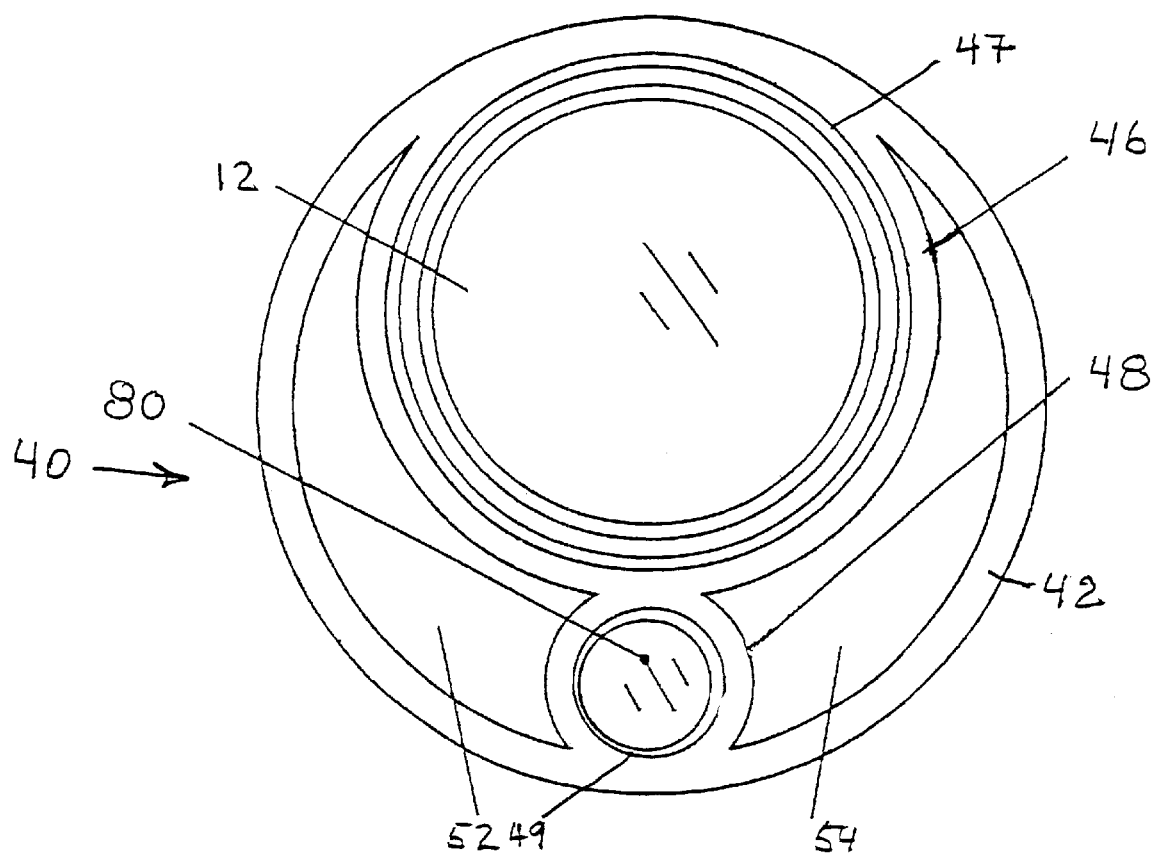
FIG. 5 is an enlarged cross sectional view of another embodiment of the invention taken along line 4'—4' on FIG. 3.

The present invention is directed towards a micro-endoscope assembly 10 which can be used and inserted into the lactiferous ducts 100 of the breast of a woman patient and a method for intraductal brachytherapy. The lactiferous ducts generally range in number from about six to about twelve in women and lead from areas of the breast to the nipple where they are in parallel vertical orientation with each other. The ducts have a very thin cell wall ranging from 3 to 4 cells in thickness and are resilient. The ducts have a smooth inner surface and white color which resemble visually the interior of a standard PVC pipe.

The best mode and preferred embodiment of the invention is shown in FIGS. 1–4. The micro assembly 10 consists of tube or guide cannula 14 which seats and guides the endoscope 12. The cannula 14 has an outer cylindrical wall 16 which defines an internal passageway which runs along its length to seat and guides the endoscope 12. Cannula tube 14 may be a rigid steel tube ranging from 5–20 cm long having an outer diameter ranging from 0.5 mm to approximately 1.2 mm or alternatively may be a semi-rigid tube made of flexible or transparent plastic, or some other suitable material, and having the same or a longer length. The exterior of the cannula is marked with marking indicia 15 as seen in FIG. 3 so that the depth of penetration of the micro-endoscope assembly into the duct can be noted as well as the distance of the tip from the cancerous tissue. The marking indicia can be in the form of rings of opaque, translucent or light reacting material or any other suitable geometry which is easily visible to the surgeons eye. The marking indicia can be printed onto the outer surface of the cannula or imbedded in the cannula structure material. Various cannula are envisioned to be interchangeable with the endoscope 12 by unscrewing one guide cannula from the endoscope front hub 18 and its associated connector member 20 and screwing one another on to the connector member.

The endoscope 12 is provided with tube body 17 formed with objective lens at its distal end. The endoscope 12 has a proximal end in the form of a back member 26 having a light post 27 and a video port 29 as seen in FIG. 2.

Figure 6:
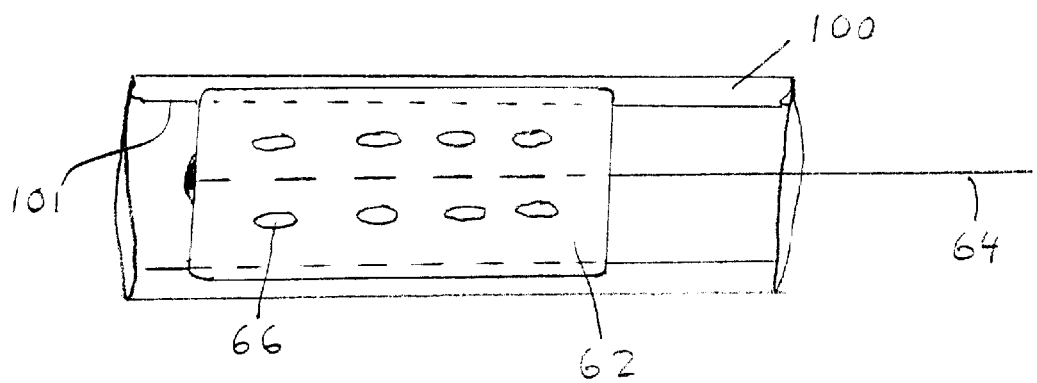
FIG. 6 is an enlarged cross sectional view of a seed cartridge used in the invention deposited in a mammary duct.
Figure 7:
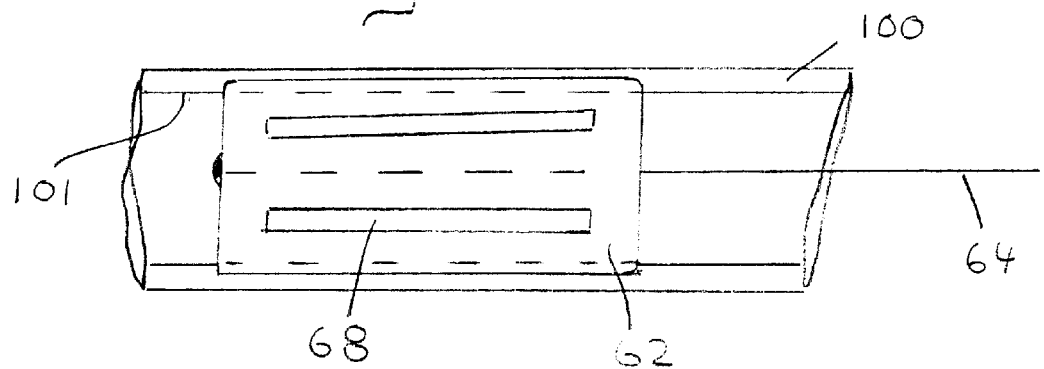
FIG. 7 is an enlarged cross sectional view of an alternate embodiment rod cartridge used in the invention.
Figure 8:
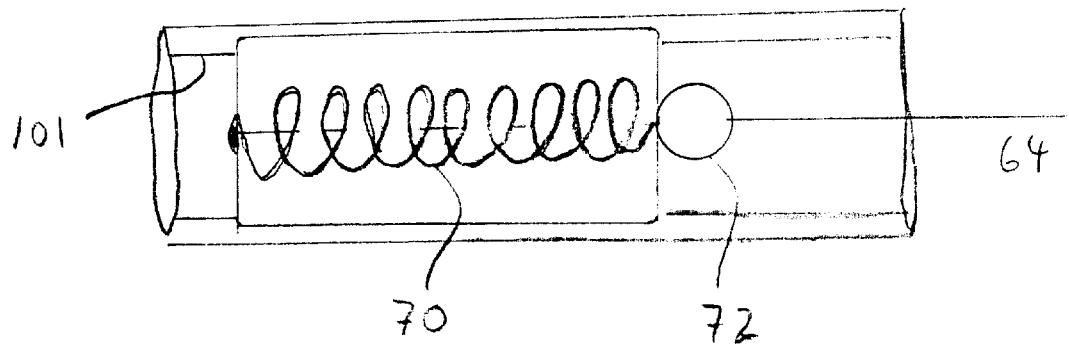
FIG. 8 is an enlarged cross sectional view of another alternate embodiment cartridge containing a coil and eyelet used in the invention.

The preferred cannula embodiment 30 has a cylindrical outer cannula or sheath 32 formed with a beveled distal end 34 as shown in FIG. 3 or a cylindrical end. The inner wall of sheath 32 defines a cylindrical inner channel 33 which has an inner cylindrical tube 36 eccentrically mounted thereon. The tube 36 defines the endoscope channel 37 and holds endoscope 12. The inner cylindrical tube 36 is eccentrically mounted in cylindrical inner channel 33 to the wall of the cannula sheath 32 and its outer surface together with the inner surface of the sheath or tube 32 to define a moon shaped channel 38 which acts as a channel or passageway providing irrigation and aspiration and is also used as a port through which a cartridge or cannister 60 can be inserted using a plunger mechanism 80 having a length longer than sheath 32 to engage the cartridge moving it along the cannula passageway until it reaches the patient's duct area to be treated at which time it is discharged from the cannula into the duct. The cartridge body 62 is secured to strand 64 which be knotted at the distal end of the body 62 as seen in FIG. 6 or otherwise secured to the body with the proximal end of the strand being located outside of the breast and taped to the nipple after insertion of the cartridge. After treatment the cannula is reinserted into the duct with the strand occupying the passageway 38 allowing the surgeon to pull the cartridge 60 back into the channel 38 with the cartridge 60 and cannula sheath 32 being removed from the breast.

Suitable materials which can be used for the cartridge body 62 include polyvinyl acetal, collagen, fibrin, gelatin or other suitable biocompatible binders which hold the seed 66 or a construct such as a rod 68, coil 70 and eyelet 72 in an orientated position. The preferred body material is constructed of compressed polyvinyl acetal (PVA) material having a controlled pore size uniformly distributed throughout its volume which is fast wicking and has a high liquid holding capacity. The material has an instantaneous absorbency time and expands uniformly to absorb fluid in a range of 23–27 times the sponge weight. The expanded body engages with the inner wall 101 of the duct 100 and stays in a fixed position in the duct without injury to the patient while allowing easy removal. If desired the body 62 can be hydrated with radiation absorbing salts or chemotherapy drugs.

The rod 68, coil 70 and eyelet 72 can be constructed of a source wire of nitinol (nickel-titanium alloy) with a radioisotope source material such as Ir-192 sealed therein. The source wire may be composed of stainless steel, platinum or other material of suitable flexibility and other source materials which can be used include cobalt, cesium, palladium, gold and iodine.

Suitable working devices in the form of seeds 66 that can be inserted in the cartridge body 62 include small containers or plugs containing radioactive seeds. The term "radioisotope" refers to naturally or non-naturally occurring water insoluble radioisotopes conventionally employed in nuclear medicine including, by way of example only, Yttrium 90 (.sup.90yttrium), Iridium 192 (.sup.192iridium), Iodine 125 (.sup.125iodine), Cobalt 60 (.sup.60cobalt), Magnesium 52 (.sup.52magnesium), Phosphorus 32 (.sup.32phosphorus0), and Strontium 90 (.sup.90strontium).

The term "absorbed dose" or "radiation dose" refers to the dose of radiation typically employed by the attending oncologist in treating cancerous tissue or tumors. The radiation dose is defined in terms of energy deposited per unit mass, given in the following units: 1 Gray (Gy)=1 Joule per kilogram. In the past, the standard unit of radiotherapy was 1 rad, and 1 Gy=100 rads.

The polymer or prepolymer compositions employed in this invention are prepared by conventional methods whereby each of the components is added and the resulting composition mixed together until the overall composition is substantially homogeneous. Likewise gelatin, fibrin and collagen are premolded.

The radioisotope implant can be added to the composition and the composition is cured and dried and compressed into the form used in the invention.

Treatment dosages of radiation employed in a particular patient are, of course, dependent upon the judgment of the attending clinician and nuclear medicine professional depending upon factors such as the type and severity of the abnormality in the patient, the age, weight and general condition of the patient, the toxicity and/or side effects due to the radiation treatment and the like. Such factors are well known to the skilled artisan.

The distal portion of the working endoscope device allows the cannister or cartridge 60 delivery device to be positioned either contacting or in close proximity to an abnormal tissue site inside the duct 100 while energy is delivered from outside the site to the cartridge or by the readioisotope through the cartridge. The deposited cartridge thus allows energy to be delivered to the abnormal tissue site with minimal surrounding tissue destruction.

An alternate embodiment of the cannula 40 is shown in cross section in FIG. 5. This embodiment has a cylindrical outer cannula or sheath 42 which defines a cylindrical inner channel 43 in which an inner cylindrical tube 46 is eccentrically mounted to the wall of sheath 42. The cylindrical tube 46 defines the endoscope channel conduit 47 to hold the endoscope 12. A second smaller cylindrical tube 48 is eccentrically mounted in channel 43 adjacent to and integral with a portion of the wall of tube 46 and a wall of the cannula 42 to form an cartridge channel 49 which holds the cartridge 60 and cartridge plunger mechanism 80. The cylindrical tube structure 46 divides the moon shaped channel up into two separated segments 52 and 54 which serve as the irrigation for the cartridge in the form of chemotherapy fluid or a radioisotope salt carried by liquid. Excess fluid can then be aspirated back from the site through the cannula.

FIG. 1 also shows the endoscope 12 with the lens tube 17 and tube portion 19 coupled between hub 18 and back end 26. Tube 19 includes a passageway in it's interior capable of holding fiber optic strands and/or illumination strands. Such strands run from video port 29, through tube portion 19 into hub 18. The strands run through hub 18 into the inner passageway of tube portion 17 though or outside of the working channel, as described in more detail below. These strands provide both a light source to the area of interest and a video source to the video port, allowing the physician to see an image of the area of the duct where the cartridge 60 is to be deposited. The back end 26 is formed with a light source post connector 27. The tube portion 14 which has an outer diameter of approximately 1.2 mm has a working channel, a plurality of light fibers and a lens. The light fibers 22 which are commercially obtainable run the length of the guide tube 17 and provide light to the areas of interest. The tube cannula 14 can alternately carry the light fibers or have them molded in the tube material. The lens also runs longitudinally down inner passage of guide tube 17.

Because the cannula tube is of such a small outer diameter, the physician can manipulate the tube from the proximal end in order to place the end of the tube with the cartridge 60 projecting therefrom adjacent the diseased tissue which is being treated.

In operation of the micro-endoscope assembly 10, the rigid guide tube 14 is placed in a lactiferous duct in the patients breast after the nipple has been numbed The physician can view the interior of the duct, which has a white smooth surface, as the endoscope passes on its way through the duct to the area of interest which has an abnormal appearance and is found by watching the screen attached to video monitor. Once the duct area of interest or cancer is reached, the physician can manipulate the cannula tube end 34 to orient the cartridge 60 adjacent the tissue to be treated. Plunger 80 is inserted into the cannula passageway and pushes the cartridge 60 into duct 100 adjacent the diseased tissue area. The cannula is irrigated with saline, a chemotherapy fluid or a radioisotope salt solution to hydrate the cartridge body causing it to swell and be seated in the duct 100. The excess fluid is aspirated away and the cannula is removed from the duct and nipple leaving the end of the strand 64 distal from that portion secured to the body 62 hanging outside of the nipple where it is taped off and later reinserted in the cannula passageway when the cannula is reinserted into the nipple and duct. The strand is pulled and the cartridge moves into the passageway and the entire assembly is removed from the duct and breast.

The principles, embodiments and modes of operation of the present invention have been described in the foregoing specification. The invention that is sought to be protected herein, however, is not to be considered as limited to the particular forms disclosed, since these are to be regarded as illustrative rather than restrictive. Variations and changes may be made by those skilled in the art without departing from the spirit and scope of the invention. For example, the present invention is not limited to the particular dimensions or uses described, except as explicitly defined in the claims. Instead, the embodiments described here should be regarded as illustrative rather than restrictive. Variations and changes may be made by others without departing from the scope of the present invention as defined by the following claims.

What I claim is:

1. A micro-endoscope assembly for intraductal brachytherapy of a mammary duct comprising a cylindrical guide tube having a diameter ranging from 0.5 mm to about 1.2 mm defining an internal passageway, a relatively smaller cylindrical tube eccentrically formed in said cylindrical passageway of a diameter smaller than said tube internal cylindrical passageway to receive and guide an endoscope assembly, said smaller cylindrical tube forming together with an inner wall surface of said cylindrical guide tube at least a second passageway, an endoscope mounted in said smaller cylindrical tube, a plunger member movably mounted within said second passageway adapted to move a cartridge treated to produce localized radiation adjacent tissue which is to be treated in said mammary duct; wherein said cartridge has a body which is constructed of compressed dry polyvinyl acetal with an absorption rate of at least 20 times the weight of the material.

2. A micro-endoscope assembly as claimed in claim 1 wherein said cartridge has at least one seed mounted therein.

3. A micro-endoscope assembly as claimed in claim 1 wherein said cartridge has at least one rod mounted therein.

4. A micro-endoscope assembly as claimed in claim 1 wherein said cartridge has at least one coil mounted therein.

5. A micro-endoscope assembly as claimed in claim 1 wherein said cartridge has a stem and eyelet mounted therein.

6. A micro-endoscope assembly for intraductal brachytherapy of a mammary duct comprising a cylindrical guide tube having a diameter ranging from 0.5 mm to about 1.2 mm defining an internal cylindrical passageway a relatively smaller cylindrical tube eccentrically formed in said cylindrical passageway having a diameter smaller than said tube internal cylindrical passageway to receive and guide an endoscope, said smaller cylindrical tube forming together with an inner wall surface of said cylindrical guide tube at least a second passageway, and an endoscope mounted in said smaller cylindrical tube, a second conduit of a smaller diameter than the smaller cylindrical tube is mounted in said at least second passageway to divide said at least a second passageway into two separate divided sections and a plunger member movably mounted within said second passageway adapted to move a cartridge which can be treated to produce localized radiation adjacent tissue to be treated in said mammary duct; wherein said cartridge has a body which is constructed of compressed dry polyvinyl acetal.

7. A micro-endoscope assembly as claimed in claim 6 wherein said cartridge has at least one seed containing a radioisotope mounted therein.

8. A micro-endoscope assembly as claimed in claim 6 wherein said cartridge has at least one rod containing a radioisotope mounted therein.

9. A micro-endoscope assembly as claimed in claim 6 wherein said cartridge has at least one coil containing a radioisotope mounted therein.

10. A micro-endoscope assembly as claimed in claim 6 wherein said cartridge has a stem and eyelet containing a radioisotope mounted therein.

11. A method of intraductal brachytherapy in the mammary duct of a woman's breast using a micro-endoscope assembly having a cylindrical cannula with a distal end with a diameter ranging from 0.5 mm to about 1.2 mm, the method comprising the steps of:

(a) inserting the distal end of the micro-endoscope assembly through a nipple of a breast of a woman patient into the mammary duct of a woman patient;

(b) viewing the interior of the duct until an area of abnormal tissue to be treated is ascertained;

(c) positioning the micro-endoscope assembly proximate the abnormal tissue;

(d) discharging a cartridge containing means which can be treated to produce localized radiation from said micro-endoscope assembly past the distal end of the assembly until it is seated in said mammary duct in proximity to said area of abnormal tissue to be treated; and (e) withdrawing said micro-endoscope assembly from said mammary duct, wherein said cartridge containing means to produce localized radiation is removed from said breast duct by the steps of (f) reinserting said micro-endoscope assembly into said mammary duct;

(g) placing said cartridge into said micro-endoscope assembly and (h) removing said micro-endoscope assembly from said mammary duct.

12. A method of intraductal brachytherapy in a mammary duct with a cannula assembly having a diameter ranging from about 0.5 mm to about 1.2 mm, said cannula assembly having a body with distal end, a proximal end, and defining a conduit for receiving a container which can be treated to produce localized radiation comprising the steps of:

(a) placing said container into a passageway formed in the body of said cannula assembly (b) inserting a distal end of the cannula assembly into the mammary duct of the breast of a woman patient to view the duct for an area of abnormal tissue to be treated;

(c) positioning the distal end of the cannula assembly in an area proximate the abnormal tissue;

(d) placing said container assembly into said mammary duct proximate tissue to be treated;
(e) irrigating said breast duct area to cause said container body to swell and be seated in said breast duct;
(f) removing said cannula assembly from said mammary duct leaving said container seated in said mammary duct.

13. A method as claimed in claim 12 wherein said container body is irrigated with a fluid chemotherapy agent.

14. A method as claimed in claim 12 wherein said container body is irrigated with radioisotope salts in a fluid carrier.

* * * * *